US00PP34892P2

(12) United States Plant Patent
Thiede

(10) Patent No.: US PP34,892 P2
(45) Date of Patent: Jan. 3, 2023

(54) ***DIANTHUS* PLANT NAMED 'KLEDP21367'**

(50) Latin Name: ***Dianthus caryophyllus* L.**
Varietal Denomination: KLEDP21367

(71) Applicant: Klemm+Sohn GmbH & Co. KG, Stuttgart (DE)

(72) Inventor: Lena Thiede, Riederich (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/735,828

(22) Filed: May 3, 2022

(51) Int. Cl.
*A01H 5/02* (2018.01)
*A01H 6/30* (2018.01)

(52) U.S. Cl.
USPC ..... Plt./277
CPC ..... *A01H 6/305* (2018.05)

(58) Field of Classification Search
USPC ..... Plt./276, 277
CPC ..... A01H 5/02
See application file for complete search history.

(56) References Cited

PUBLICATIONS https://www.floraldaily.com/article/9305098/new-dianthus-early-spring-crops-catalogue-2021/; Mar. 23, 2021; 3 pages.*
https://www.gasagroup.com/Files/Images/corporate_website/Young%20Plants/Catalogues/Selecta-Dianthus-Early-Spring.pdf; May 19, 2022; 2 pages.*

* cited by examiner

*Primary Examiner* — Kent L Bell
(74) *Attorney, Agent, or Firm* — Weatherly IP Solutions, LLC; Barbara Campbell

(57) ABSTRACT

A new *Dianthus* plant designated 'KLEDP21367' particularly distinguished by double pink flowers having darker pink macules and a medium-compact habit, is disclosed.

1 Drawing Sheet

Genus and species: *Dianthus caryophyllus* L.
Variety denomination: 'KLEDP21367'.

BACKGROUND OF THE NEW PLANT

The present invention comprises a new and distinct variety of *Dianthus*, botanically known as *Dianthus caryophyllus* L., and hereinafter referred to by the variety name 'KLEDP21367'. 'KLEDP21367' originated from a controlled cross conducted in 2013 in Stuttgart, Germany between the proprietary *Dianthus* female parent 'KLEDP11109' (Unpatented) and the *Dianthus* male parent 'DCP-2012-0022' (Unpatented). The seeds from this cross were sown in Stuttgart, Germany and a single plant was selected in May 2015.

In August 2015, 'KLEDP21367' was first vegetatively propagated by vegetative stem cuttings in Stuttgart, Germany. 'KLEDP21367' was found to reproduce true to type in successive generations of asexual propagation in Stuttgart, Germany via vegetative cuttings.

SUMMARY

The following are the most outstanding and distinguishing characteristics of 'KLEDP21367' when grown under normal horticultural practices in Latina, Italy and Stuttgart, Germany.

1. Pink, double flowers having dark pink macules; and
2. A medium-compact habit.

DESCRIPTION OF THE PHOTOGRAPH

This new *Dianthus* plant is illustrated by the accompanying photograph of a 14-week-old plant taken in March 2019 and grown in a greenhouse in Stuttgart, Germany. The colors shown are as true as can be reasonably obtained by conventional photographic procedures. The photograph is a whole plant photo of 'KLEDP21367' and shows the foliage, buds, and flowers.

DESCRIPTION

The following detailed descriptions set forth the distinctive characteristics of 'KLEDP21367'. The data which define these characteristics were collected from asexual reproductions carried out in Latina, Italy. Data was collected in March 2022 from plants that were potted in week 41 in 2021 and grown in a greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus* L.
- *Designation*.—'KLEDP21367'.
- *Type*.—Pot carnation.

Parentage:
- *Female parent*.—*Dianthus* 'KLEDP11109' (Unpatented).
- *Male parent*.—*Dianthus* 'DCP-2012-0022' (Unpatented).

Plant:
- *Propagation type*.—Vegetative stem cuttings.
- *Time to produce a rooted young plant*.—28 days.
- *Root description*.—Fine and RHS 155C (White).
- *Rooting habit shape*.—Lanceolate.
- *Plant form and habit*.—Upright and medium-compact.
- *Plant height*.—8.0 cm.
- *Plant diameter or spread*.—13.0 cm.

Lateral branches/stems:
*Shape of the branch in cross-section.*—Circular.
*Hollowness of the branch.*—Absent.
*Length.*—9.0 cm.
*Diameter.*—0.3 cm.
*Internode length.*—1.3 cm.
*Internode quantity per branch.*—5.
*Node length.*—0.3 cm.
*Node diameter.*—0.7 cm.
*Texture.*—Smooth.
*Color.*—RHS 149D (Yellow-Green).
*Flower clustering on the lateral branch.*—In all lateral branches.

Foliage:
*Arrangement.*—Opposite.
*Length.*—7.6 cm.
*Width.*—0.8 cm.
*Shape.*—Obovate.
*Apex.*—Acute.
*Base.*—Obtuse.
*Margin.*—Entire.
*Texture (both upper and lower surfaces).*—Smooth.
*Cross-section of the leaf.*—Weakly concave.
*Curvature of the leaf.*—Absent.
*Glaucosity of the leaf.*—Weak.
*Leaf color (both immature and mature).*—Upper surface: RHS 137B (Green) for immature and RHS 139A (Green) for mature. Lower surface: RHS 137D (Green) for immature and RHS N137C (Green) for mature.
*Venation pattern.*—Absent.

Flowers:
*Flower type.*—Double flowers with sprays; 7 flowers per spray.
*Fragrance.*—Present.
*Position of the flowers compared to the foliage of the plant.*—Same level.
*Profile of both the upper and lower part in the lateral view.*—Convex.
*Diameter of the flower.*—4.5 cm.
*Natural flowering season.*—Spring to Autumn.
*Flower longevity on the plant.*—14 days.

Buds:
*Length.*—2.7 cm.
*Diameter.*—0.7 cm.
*Shape.*—Elliptic.
*Color.*—RHS 137B (Green).
*Extrusion of the styles at the bud stage.*—Absent.

Corolla:
*Quantity of petals and arrangement.*—28 and arranged in 3 whorls.
*Corolla height.*—3.5 cm.
*Petal length.*—3.5 cm.
*Petal width.*—1.9 cm.
*Petal shape.*—Obtuse.
*Petal apex.*—Obtuse.
*Petal base.*—Acute.
*Petal margin.*—Crenate.
*Depth of petal margin.*—Shallow.
*Petal texture (both upper and lower surfaces).*—Smooth.
*Petal color.*—Immature: Upper surface: RHS N74A (Red-Purple). Lower surface: RHS 71C (Red-Purple). Mature: Upper surface: RHS 72C (Red-Purple) with RHS 61A (Red-Purple) macules being 0.1 cm in width. Lower surface: RHS N74C (Red-Purple).
*Calyx.*—Quantity of sepals: Composed of 5 sepals. Longitudinal axis of the lobes of the calyx: Straight. Shape: Acute. Calyx height: 2.3 cm. Calyx diameter (at the apex): 1.4 cm. Sepal texture (both upper and lower surfaces): Smooth. Sepal color: Upper surface: RHS 143A (Green). Lower surface: RHS 144D (Green). Position of the outer lobes of the epicalyx in relation to the calyx: Adpressed. Apex shape of the outer lobes of the epicalyx: Acute. Tip length of the outer lobes of the epicalyx: 0.1 cm. Apex shape of the inner lobes of the epicalyx: Short acuminate. Tip length of the inner lobes of the epicalyx: 0.1 cm.

Peduncles:
*Length.*—0.8 cm.
*Diameter.*—0.3 cm.
*Strength.*—Strong.
*Texture.*—Smooth.
*Color.*—RHS 139A (Green).

Reproductive organs:
*Stamens.*—Quantity per flower: 9. Filament length: 0.7 cm. Filament color: RHS 155A (White). Anther length: 0.2 cm. Anther diameter: Less than 0.1 cm. Anther color: RHS 12C (Yellow). Pollen amount: None observed to date.
*Pistils.*—Quantity per flower: 3. Length: 1.1 cm. Diameter: 0.1 cm. Stigma: Color: RHS 71B (Red-Purple). Shape: Filamentous. Length: 0.1 cm. Diameter: 0.1 cm. Style: Color: RHS NN155A (White). Length: 1.0 cm. Diameter: 0.1 cm. Ovary: Color: RHS N144D (Yellow-Green). Width: 0.7 cm.

Fruit and seed set: None observed to date.

Disease and pest/insect resistance: No disease and pest/insect resistance observed.

COMPARISON WITH PARENTAL LINES AND KNOWN VARIETY

'KLEDP21367' is distinguished from the parents as described in Table 1.

TABLE 1

Comparison with Parental Lines

| Characteristic | 'KLEDP21367' | Female parent 'KLEDP11109' | Male parent 'DCP-2012-0022' |
|---|---|---|---|
| Flower filling | Filled | Semi-filled | Good filled |
| Branching | Good branching | Very good branching - more than 'KLEDP21367' | Medium branching - more than 'KLEDP21367' |

'KLEDP21367' can be compared to the commercial *Dianthus* variety 'KLEDP07089' (Unpatented). Differences between the varieties are described in Table 2.

TABLE 2

Comparison with Similar Variety

| Characteristic | 'KLEDP21367' | 'KLEDP07089' |
|---|---|---|
| Earliness to flower | Medium-late | Very early |
| Plant height | Medium-compact | Compact |
| Flower filling | Filled | Semi-filled |

I claim:

1. A new and distinct variety of *Dianthus* plant designated 'KLEDP21367' as illustrated and described herein.

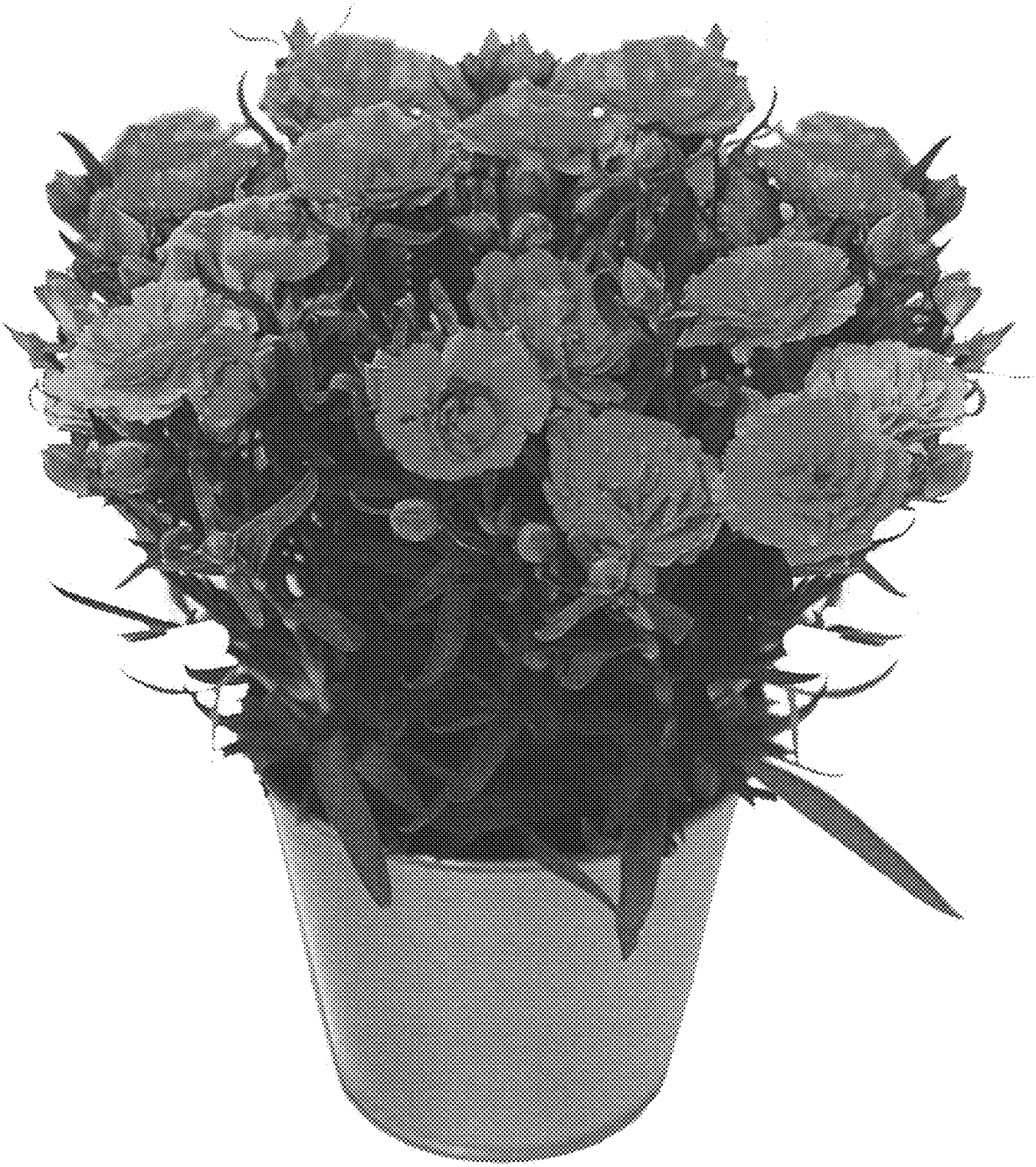

* * * * *